US00PP08922P

United States Patent [19]

Zaiger et al.

[11] Patent Number: Plant 8,922

[45] Date of Patent: Oct. 4, 1994

[54] PLUM COT TREE "FLAVORGLO"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 189,034

[22] Filed: Jan. 31, 1994

[51] Int. Cl.[5] ..... A01H 5/00

[52] U.S. Cl. ..... Plt./38.1

[58] Field of Search ..... Plt. 38.1

*Primary Examiner*—James R. Feyrer

[57] ABSTRACT

A new and distinct variety of Plum Cot tree (plum×apricot) which has the unique combination of desirable features that are outstanding in a new variety:

1. Fruit with excellent flavor and eating quality.
2. Regular and moderate production of large size fruit.
3. Fruit with firm flesh.
4. Vigorous semi-upright growth.
5. Fruit ripening in the early maturity season.
6. Bearing fruit with an attractive yellow skin color.

1 Drawing Sheet

ORIGIN OF THE VARIETY

The present new variety of Plum Cot tree was originated by us in our experimental orchard located near Modesto, Calif., as a selected seedling from an open pollinated, early maturing plum selection with the field identification No. 35EA376. The seedling 35EA376 was selected from a large group of open pollinated Red Beaut Plum (U.S. Plant Pat. No. 2,539) seedlings. A large number of seedlings were grown and maintained under close observation and the present plum cot variety evidenced the distinctive desirable fruit characteristics described above and was selected for asexual reproduction and commercialization.

ASEXUAL REPRODUCTION OF THE VARIETY

The present and distinct new variety of plum cot tree was asexually reproduced by budding, as performed by us in our experimental orchard located near Modesto, Calif., and the asexually propagated trees show that all characteristics of the tree and its fruit are established and transmitted through succeeding propagations and come true to the original tree.

SUMMARY OF THE VARIETY

A new and distinct variety of plum cot tree which is of large size, vigorous, semi-upright growth and a regular bearer of large, firm, yellow flesh, clingtone fruit with excellent flavor and eating quality. The tree is further characterized by being moderately productive (usually little to no thinning is necessary), producing fruit that is relatively uniform in size throughout the tree and having an attractive yellow skin color. In comparison to Flavorella Plum Cot (U.S. Plant Pat. No. 8,470) the fruit is larger in size and matures approximately 7 days earlier.

BRIEF DESCRIPTION OF THE PHOTOGRAPHS

The accompanying color photographic illustrations show typical specimens of the fruit and foliage of the present new plum cot variety with the upper and lower surface of the leaves being illustrated and the exterior and sectional view of the fruit being shown to expose flesh coloration with a stone remaining in place. The photographs were taken shortly after being picked at maturity (firm ripe) and the colors are as nearly true as is reasonably possible in a color representation of this type.

DESCRIPTION OF THE VARIETY

The following is a detailed botanical description of the present new and distinct variety of plum cot tree, its flowers, foliage and fruit as based on observations of specimens grown near Modesto, Calif., with color terminology (except those in common terms) in accordance with Reinhold Color Atlas by A. Kornerup and J. H. Wansher.

Tree:
- *Size.*—Large.
- *Density.*—Medium dense.
- *Vigor.*—Vigorous.
- *Form.*—Semi-upright.
- *Bearer.*—Regular.
- *Production.*—Moderate.

Trunk:
- *Size.*—Large.
- *Texture.*—Medium shaggy.
- *Color.*—Brown to leather brown (6-E-5) to (6-E-6).

Branches:
- *Size.*—Medium.
- *Surface.*—Smooth to medium shaggy, varies with age of growth.
- *Lenticels.*—Numerous. Large size.
- *Color.*—Light brown to brown (6-D-6) to (6-D-7).

Leaves:
- *Size.*—Large. Average length — $4\frac{3}{4}''$. Average width — $2\frac{1}{4}''$.
- *Form.*—Elliptic. Pointed.
- *Thickness.*—Medium.
- *Texture.*—Smooth.
- *Margin.*—Serrate.
- *Petiole.*—Average length — $1\frac{1}{8}$. Medium thickness.
- *Glands.*—Size — small. Average number 2, varies from 1 to 3. Globose. Positioned on lower portion of leaf blade and upper portion of petiole.
- *Color.*—Upper surface — green to dark green (28-E-5) to (29-F-5). Lower surface — grayish green to green (28-E-4) to (28-D-4).

Flower buds:
- *Size.*—Medium.

*Form.*—Plump.
*Length.*—Medium.
*Pubescence.*—Pubescent.

Flowers:
*Size.*—Medium.
*Blooming period.*—Feb. 19, 1993 to Feb. 27, 1993. Varies slightly due to climatic conditions.
*Pollen.*—Present.
*Color.*—White.

Fruit:
*Maturity when described.*—Firm ripe.
*Date of first picking.*—May 22, 1993.
*Date of last picking.*—May 27, 1993. Varies with climatic conditions.
*Size.*—Large. Average diameter axially — $2\frac{5}{8}''$. Average transversely in suture plane — $2\frac{5}{8}''$.
*Form.*—Nearly globose — varies from globose to slightly elongated.
*Suture.*—Very shallow, extends from base to apex.
*Ventral surface.*—Nearly rounded, very slight depression.
*Apex.*—Slightly depressed, very small apical point in base of depression.
*Base.*—Retuse.
*Cavity.*—Rounded to slightly elongated in suture plane. Average depth — $\frac{1}{2}''$. Average breadth — $\frac{5}{8}''$.

Skin:
*Thickness.*—Medium.
*Texture.*—Medium, tenacious to flesh.
*Tendency to crack.*—None.
*Down.*—Moderate, short.
*Color.*—Yellow to apricot yellow (5-B-6) to (5-B-7).

Flesh:
*Texture.*—Firm.
*Ripens.*—Evenly.
*Fibers.*—Small, tender.
*Amygdalin.*—Undetected.
*Flavor.*—Excellent, good balance between acid and sugar with a creative taste between plum and apricot.
*Juice.*—Moderate.
*Aroma.*—Moderate.
*Eating quality.*—Excellent.
*Color.*—Cream yellow to golden yellow (4-A-6) to (5-A-4).

Stone:
*Type.*—Clingstone.
*Size.*—Medium. Average length — 1 3/16". Average width — $\frac{3}{4}''$. Average thickness — $\frac{1}{2}''$.
*Form.*—Ovoid.
*Base.*—Usually rounded, varies from rounded to straight.
*Apex.*—Usually rounded, varies from rounded to slight point.
*Sides.*—Nearly equal, varies from equal to unequal.
*Surface.*—Pitted throughout, pit cavities vary from elongated to round.
*Tendency to split.*—None.
*Color.*—Varies from light brown to brownish red (7-C-6) to (8-C-6).

Use:
*Market.*—Local and long distance. Dessert.

Keeping Quality: Good.
Shipping quality: Good.

The present variety, its flowers, foliage and fruit herein described may vary in slight detail due to cultural practices, soil types and climatic conditions under which the variety may be grown; the present description is that of the variety grown under the ecological conditions prevailing near Modesto, Calif.

We claim:

1. A new and distinct variety of Plum Cot tree, as illustrated and described, characterized by its large size, vigorous, semi-upright growth and a moderately productive and regular bearer of firm, yellow flesh, clingstone fruit with excellent flavor and eating quality; the fruit is further characterized by being of large size, nearly uniform throughout the tree and in comparison to the Plum Cot Flavorella (U.S. Plant Pat. No. 8,470) the fruit is larger in size and matures approximately 7 days earlier.

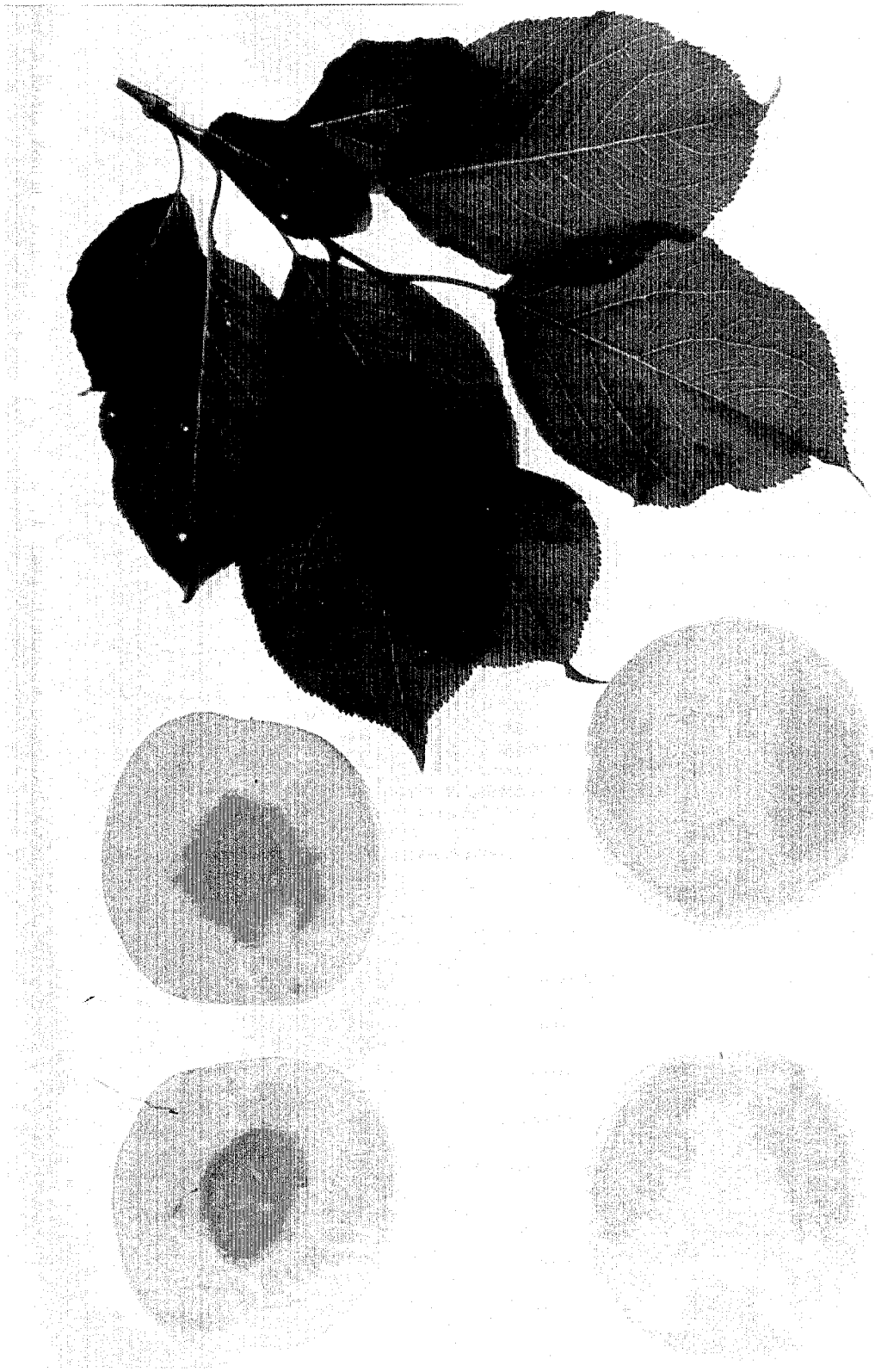

* * * * *